(12) United States Patent
Goldring et al.

(10) Patent No.: US 10,012,585 B2
(45) Date of Patent: Jul. 3, 2018

(54) GAS SAMPLING CELL

(71) Applicant: ORIDION MEDICAL 1987 LTD., Jerusalem (IL)

(72) Inventors: Alon Goldring, Tel Aviv (IL); Alon Sasson, Rehovot (IL); Avner Bar-Lev, Givatayim (IL); Gershon Levitsky, Jerusalem (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 0 days.

(21) Appl. No.: 14/880,280

(22) Filed: Oct. 12, 2015

(65) Prior Publication Data
US 2017/0102322 A1   Apr. 13, 2017

(51) Int. Cl.
| G01N 21/35 | (2014.01) |
| G01N 33/00 | (2006.01) |
| A61B 5/00 | (2006.01) |
| G01N 21/3504 | (2014.01) |
| G01N 1/00 | (2006.01) |

(52) U.S. Cl.
CPC ........... *G01N 21/3504* (2013.01); *A61B 5/00* (2013.01); *G01N 1/00* (2013.01); *G01N 33/004* (2013.01); *G01N 33/0037* (2013.01)

(58) Field of Classification Search
CPC ........... G01N 21/3504; G01N 21/3103; G01N 33/0037; G01N 33/004; G01N 2201/0636; G01N 2201/061; G01N 2201/0686
See application file for complete search history.

(56) References Cited

U.S. PATENT DOCUMENTS

| 6,599,253 B1 * | 7/2003 | Baum ............... A61B 5/0813 356/303 |
| 7,488,229 B2 | 2/2009 | Ben-Oren |
| 2003/0208133 A1 * | 11/2003 | Mault ............... A61B 5/0002 600/532 |
| 2004/0162500 A1 * | 8/2004 | Kline ............... A61B 5/097 600/532 |
| 2008/0127977 A1 * | 6/2008 | Orr ............... A61B 5/0833 128/204.22 |

(Continued)

FOREIGN PATENT DOCUMENTS

| CH | WO 2015010709 A1 * | 1/2015 | ......... G01N 21/3504 |
| WO | 00/75956 | 12/2000 | |

OTHER PUBLICATIONS

Colman and Krauss (1999) Microstream capnograpy technology: a new approach to an old problem. J Clin Monit Comput 15(6): 403-9.

(Continued)

*Primary Examiner* — Mark R Gaworecki
(74) *Attorney, Agent, or Firm* — Fletcher Yoder PC

(57) ABSTRACT

A sensor for detecting concentration of a component in a breath sample including a gas sampling cell having an inlet, an outlet, a light source, a first light detector, a sampling channel configured to receive gas samples from the inlet; the sampling channel defining a light path between said light source and said first light detector; and a volume occupying material located within the sampling channel, the volume occupying material having an absorption coefficient for mid-infra-red light below 0.5 cm$^{-1}$ at room temperature.

19 Claims, 1 Drawing Sheet

(56) References Cited

U.S. PATENT DOCUMENTS

| | | | | |
|---|---|---|---|---|
| 2010/0093096 A1* | 4/2010 | Acharya | ............... | B82Y 30/00 |
| | | | | 436/4 |
| 2012/0162655 A1* | 6/2012 | Oida | ................. | G01N 21/3504 |
| | | | | 356/437 |
| 2012/0302910 A1* | 11/2012 | Freeman | .............. | A61N 1/3987 |
| | | | | 600/538 |
| 2014/0211208 A1* | 7/2014 | Patel | ..................... | G01N 21/39 |
| | | | | 356/437 |
| 2016/0151009 A1* | 6/2016 | Rudmann | ......... | G01N 21/3504 |
| | | | | 600/322 |
| 2016/0278664 A1* | 9/2016 | Pant | ...................... | A61B 5/082 |

OTHER PUBLICATIONS

Hodgkinson et al., (2013) Non-dispersive infra-red (NDIR) measurement of carbon dioxide at 4.2 μm in a compact and optically efficient sensor. Sensors and Actuators B: Chemical 186: 580-588.
Mainstream Gas Analyzers A Historical and Technological Perspective. Published by ProMed Strategies, LLC under an educational grant from PHASEIN AB, Sweden, 2009.

* cited by examiner

GAS SAMPLING CELL

TECHNICAL FIELD

The present disclosure generally relates to the field of breath sampling and gas sampling sensors.

BACKGROUND

Determination of components (e.g. $CO_2$) in a gas mixture (e.g. a breath sample) is based on the fact that gases like $CO_2$ absorb light at a specific wavelength in the infrared light spectrum. Detection of a concentration of a gas component such as $CO_2$ is therefore typically accomplished by passing a beam of infra-red light across the gas sample. Presence of $CO_2$ in the gas leads to a reduction in the amount of light in the spectrum and, based upon the reduction, the concentration of $CO_2$ in the sample is inferred.

SUMMARY

The present disclosure relates to novel gas sampling sensors for detecting concentration of a component, such as, but not limited to, $CO_2$, in a breath sample. The sensor includes a gas sampling cell having an inlet, an outlet, a light source, a first light detector, a sampling channel configured to receive gas samples from the inlet, and a volume occupying material located within the sampling channel, the volume occupying material having an absorption coefficient for mid-infra-red light below 0.5 $cm^{-1}$ at room temperature.

Advantageously, the volume occupying material located within the sampling channel of the sensor reduces the volume of the sampling cell. The reduction in sampling cell volume enables an increased discharge rate of the gas inside the cell and consequently increases the response time of the sensor, as compared to the common sampling cells. This is particularly important for high breathing rates (e.g. more than 30 breaths per minute), as is, for example, typical in infants.

Advantageously, the reduced cell volume is achieved with minimal interference with the light path between the light source and the light detector. This is due to the volume occupying material's low absorption coefficient in the absorption spectrum of the gas causing only negligible attenuation of the infrared radiation propagating through the volume occupying material.

Furthermore, due to the low absorption coefficient of the volume occupying material, the material may occupy part of the sampling channel, essentially along its entire length, such that light, emitted by the light source, reaches a first light detector (e.g. a reference light detector) basically without encountering the gas sample present in the remainder of the sampling channel. As a result, the need for a separate reference channel, sampling a reference gas, such as ambient air, is obviated. This, since emitted light propagated through the volume occupying material and detected by a reference light detector may serve as a reference to light emitted from the light source, propagated through the breath sample and detected by the main light detector. This is important since $CO_2$ tends to leak or diffuse from the main channel to the reference channel, thereby compromising the accuracy of the measurements.

According to some embodiments, the boundaries of the volume occupying material and/or the edges of the sampling channel may be coated with a reflective material. This may advantageously ensure that radiation propagating through the breath sample will be reflected back if reaching the material.

According to some embodiments, there is provided a sensor for detecting a concentration of a component in a breath sample, the sensor including a gas sampling cell including an inlet, an outlet, a light source, a first light detector, a sampling channel configured to receive gas samples from the inlet; and a volume occupying material located within the sampling channel, the volume occupying material having an absorption coefficient for mid-infra-red light below 0.5 $cm^{-1}$. According to some embodiments, the sampling channel may define an optic path between the light source and the first light detector. According to some embodiments, the component is $CO_2$.

According to some embodiments, the volume occupying material may have an absorption coefficient for mid-infra-red light below 0.3 $cm^{-1}$. According to some embodiments, the volume occupying material may have an absorption coefficient for mid-infra-red light below 0.1 $cm^{-1}$.

According to some embodiments, the volume occupying material may occupy between 25%-75% of the volume of the sampling channel. According to some embodiments, the volume occupying material may occupy between 35%-65% of the volume of the sampling channel.

According to some embodiments, the volume occupying material may include Sapphire, Silicon (Si), Germanium (Ge), Zinc Selenide (ZnSe) or any combination thereof. According to some embodiments, the volume occupying material may include Sapphire. According to some embodiments, the volume occupying material may be made of Sapphire.

According to some embodiments, the light source may be an infra-red (IR) light source.

According to some embodiments, the first light detector may include a first optical filter. According to some embodiments, the first light detector may include a second optical filter. According to some embodiments, the first optical filter may be configured to transmit light having a first wavelength; and the second optical filter may be configured to transmit light having a second wavelength.

According to some embodiments, the gas sampling cell may further include a reference light detector. According to some embodiments, the reference light detector may include a first and a second optical filter. According to some embodiments, the first optical filter may be configured to transmit light having a first wavelength, and the second optical filter may be configured to transmit light having a second wavelength.

According to some embodiments, the path length between the light source and the first light detector and/or the reference light detector may be in the range of 5-15 mm.

According to some embodiments, the distance between a first end of the volume occupying material and the light source may be less than 5 mm. According to some embodiments, the distance between a second end of the volume occupying material and the first light detector and/or the reference light detector may be less than 5 mm.

According to some embodiments, the wall of the volume occupying material may be covered with a reflective material. According to some embodiments, the wall of the sampling channel may be covered with a reflective material.

According to some embodiments, the sensor may have a response time of less than 100 ms.

According to some embodiments, the gas sampling cell may be devoid of a reference channel.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1A:
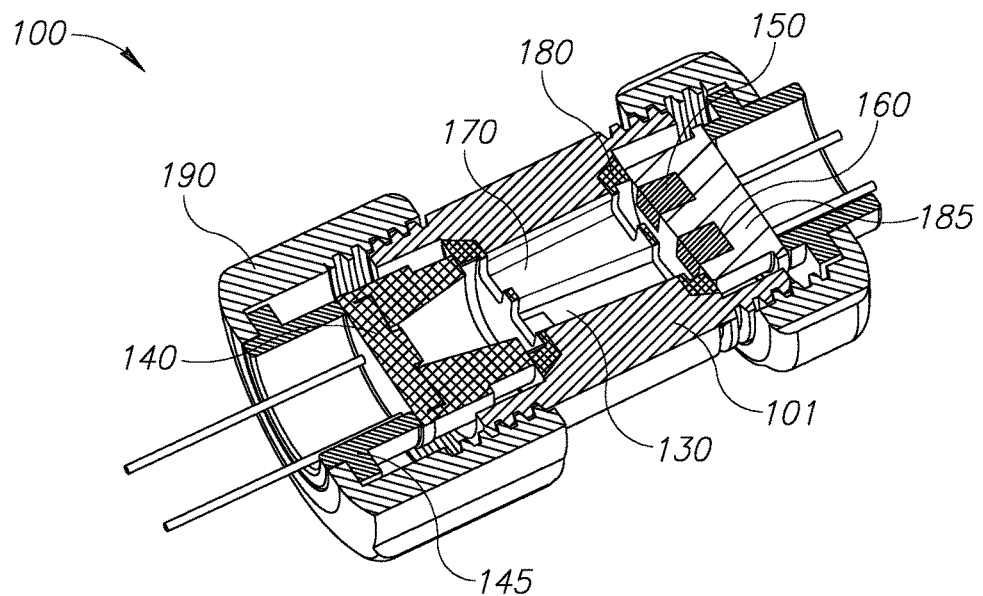
FIG. 1A and FIG. 1B schematically illustrate cross-sectional views of a gas sampling cell, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure. Additionally, it is to be explicitly understood that any combination of any one or more of the disclosed embodiments may be applicable and is within the scope of the disclosure.

According to some embodiments, there is provided a sensor for detecting a concentration of a component in a breath sample. The sensor includes a gas sampling cell having an inlet, an outlet, a light source, a first light detector, a sampling channel and a volume occupying material having an absorption coefficient for mid-infra-red (IR) light at room temperature, which allows IR light to propagate therethrough, essentially undisturbed.

According to some embodiments, the sensor may include a carbon dioxide ($CO_2$) sensor, and the gas component may be exhaled $CO_2$. According to some embodiments, the sensor may include a nitric oxide (NO) sensor, and the gas component may include exhaled NO. According to some embodiments, the sensor is configured for side-stream capnography.

As used herein, the term "essentially undisturbed" with regards to the propagation of light may refer to light, or a spectrum thereof, being transmitted through the volume occupying material while less than 1%, less than 0.5%, or less than 0.1% thereof is absorbed. According to some embodiments, the volume occupying material may be essentially transparent to the IR light.

According to some embodiments, as used herein, the term "volume occupying material" may refer to a material positioned within a sampling channel of a gas sampling cell, thereby occupying part of the sampling channel's volume. According to some embodiments, the volume occupying material may be a material having a predetermined absorption coefficient for mid-infra-red light. According to some embodiments, the volume occupying material may have an absorption coefficient for mid-infra-red light at or below 0.5 $cm^{-1}$. According to some embodiments, the volume occupying material may have an absorption coefficient for mid-infra-red light at or below 0.3 $cm^{-1}$. According to some embodiments, the volume occupying material may have an absorption coefficient for mid-infra-red light at or below 0.1 $cm^{-1}$. According to some embodiments, the term "absorption coefficient", "attenuation coefficient" and "extinction coefficient" may be interchangeably used and refer to the distance into a material into which light of a particular wavelength can penetrate before it's intensity is reduced to 1/e of its initial value. The absorption coefficient depends on the material and on the wavelength of light, which is being absorbed. According to some embodiments, the absorption coefficient is measured at room temperature. As used herein, the term "mid-infra-red" and "mid-IR" may refer to IR with a wavelength in the range of or 3-5 μm. Each possibility is a separate embodiment.

According to some embodiments, the volume occupying material may include Sapphire, Silicon (Si), Germanium (Ge), Zinc Selenide (ZnSe) or any combination thereof. Each possibility is a separate embodiment.

According to some embodiments, the volume occupying material may be located within the sampling channel. As used herein, the term sampling channel may refer to a compartment configured to enable sampling of breath using optics. According to some embodiments, the sampling channel enables an optic path between the light source and the first light detector.

According to some embodiments, the sampling cell further includes a reference light detector. According to some embodiments, the sampling channel enables an optic path between the light source and the reference light detector.

According to some embodiments, the gas sampling cell includes only a single gas sampling channel. According to some embodiments, the sampling channel enables detection of light propagated through a breath sample (breath sampling) as well a light propagated through the volume occupying material essentially without encountering the sample (reference). According to some embodiments, breath sampling and reference measurements, may be performed simultaneously from the (single) sampling channel. According to some embodiments, the gas sampling cell may be devoid of a distinct reference sampling channel.

According to some embodiments, the volume occupying material may occupy about half of the sampling channel, such as, but not limited to, 25%-75%, 35%-65% or 40%-60% of the sampling channel. Each possibility is a separate embodiment. According to some embodiments, the volume occupying material may occupy essentially the entire optic path between the light source and the reference light detector. It is understood that due to the volume occupying material occupying about half of the sampling channel, the volume of the cell is reduced by about half compared to common sampling cells. As a result, the discharge rate of the gas inside the cell is doubled, enabling an approximately 50% reduction in the response time of the sensor. According to some embodiments, the sensor may have a response time of 200 milliseconds (ms) or less, 100 ms or less, 50 ms or less, 25 ms or less, or 15 ms or less. Each possibility is a separate embodiment. It is understood that such fast response times may be particularly advantageous when monitoring subject's with high respiration rates, such as, but not limited to, neonates and infants.

According to some embodiments, the volume occupying material may extend along the entire length (but essentially half the width) of the sampling channel. According to some embodiments, the term "length" with regards to the sampling channel may refer to the axis of the sampling channel extending from the light source to the light detector (i.e. the distance in which the light passes through the gas, also called the path length). According to some embodiments, the length of the sampling channel may be in the range of 3-15 mm, 3-10 mm, 5-15 mm or 5-10 mm. Each possibility is a separate embodiment. According to some embodiments, the length of the sampling channel may be 8 mm.

According to some embodiments, the term "essentially entire length" may refer to more than 80% of the length, more than 90% of the length, more than 95% of the length more than 98% of the length or more than 99% of the length. Each possibility is a separate embodiment. According to some embodiments, the distance between a first end of the volume occupying material and the light source may be less than 5 mm, less than 3 mm, less than 1.5 mm, less than 1 mm or less than 0.5 mm. Each possibility is a separate embodiment. According to some embodiments, the distance between a second end of the volume occupying material and the reference light detector may be less than 5 mm, less than 3 mm, less than 1.5 mm, less than 1 mm or less than 0.5 mm. Each possibility is a separate embodiment. It is understood that by minimizing the space between the volume occupying material and the light source and/or light detector, the amount of breath sample in this space, and thus the amount of $CO_2$ capable of absorbing light propagated through the volume occupying material, and thus affecting reference readings, is negligible.

According to some embodiments, the space between the volume occupying material and the light source and/or reference light detector may be filled with an optically clear adhesive (OCA) and/or an elastomeric seal. The OCA and/or the elastomeric seal may essentially eliminate the air gap between the volume occupying material and the light source and/or light detector, thereby further preventing the breath sample from affecting reference readings.

According to some embodiments, one or more walls of the volume occupying material may be covered with a reflective material, such as, but not limited to, gold. According to some embodiments, one or more walls of the sampling channel is covered with a reflective material, such as, but not limited to, gold. It is understood that by covering the walls of the volume occupying material and/or of the sampling channel with a reflective material may redirect escaping gas to the optic path between the light source and the first light detector, thereby ensuring optimal readings.

According to some embodiments, the first light detector may include a first optical filter. According to some embodiments, the filter may be configured to selectively transmit light absorbed by the component (e.g. $CO_2$) in the gas. According to some embodiments, the filter may be a bandpass filter centered at 4.26 µm. According to some embodiments, the first light detector may include a second optical filter configured to transmit light having a wavelength unaffected by the component. According to some embodiments, the second optical filter may be a bandpass filter centered at 3.95 µm.

According to some embodiments, the light source may be an infra-red (IR) light source, such as a black body, a light emitting diode or diode laser.

According to some embodiments, the first light detector and the reference detector may the same or different detector. According to some embodiments, the first light detector and the reference light detector may be the same detector. In such instance, sample and reference measurements may be made at different times or utilizing different parts of the detector. According to some embodiments, the first light detector and the reference light detector may be separate but identical detectors. According to some embodiments, the first light detector and the reference light detector may be separate but different detectors. According to some embodiments, the first light detector and the reference detector may include a same or different filter.

Figure 1B:
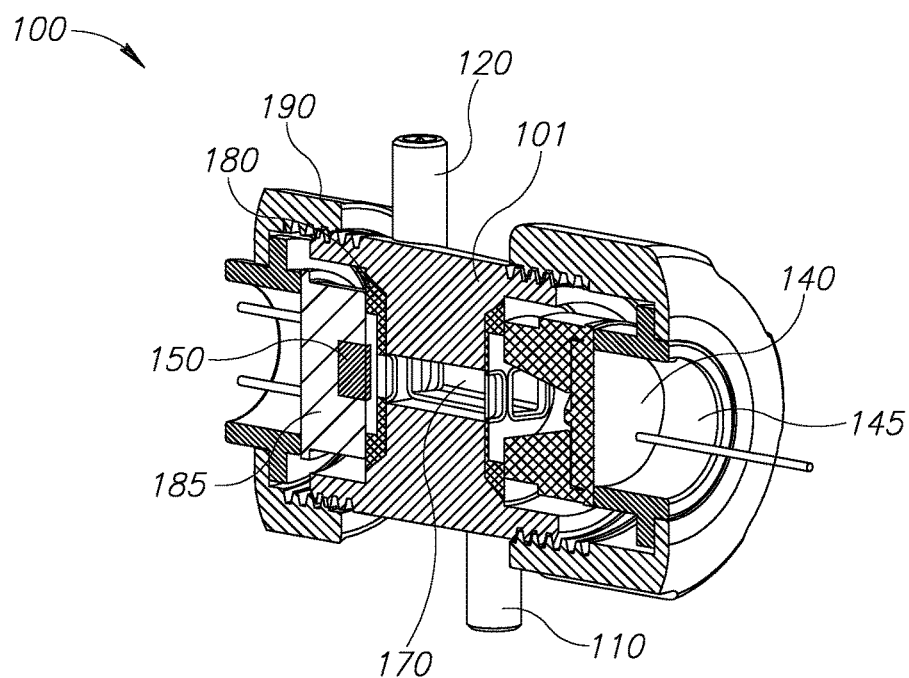

Reference is now made to FIGS. 1A and 1B, which schematically show cross-sections of a gas sampling cell 100, according to some embodiments. Gas sampling cell 100 includes a cell body 101 having an inlet 110, an outlet 120, and a sampling channel 130 configured to receive gas samples (e.g. breath samples) from inlet 110. Gas sampling cell 100 further includes a light source 140 positioned at a first end of sampling channel 130, within or in proximity to light source adaptor 145, and a detector body 185 including a main (first) light detector 150 and a reference light detector 160 at a second end of sampling channel 130. Sampling channel 130 includes a volume occupying material 170 (e.g. sapphire) located along the length of sampling channel 130 occupying the optical path between light source 140 and reference light detector 160. Consequently, light emitted by light source 140 propagates through volume occupying material 170 and reaches reference light detector 160 essentially without encountering the gas sample flowing within the gas sampling cell 100. Optionally, sampling cell 100 includes an elastomeric seal 180 configured to seal off space between volume occupying material 170 and main light detector 150 and/or reference light detector 160. Furthermore, sampling cell 100 may optionally include a tightening element 190 at least partially covering sampling cell 100. Advantageously, the remainder of sampling channel 130 configured to contain the gas sample is reduced by approximately 50%, thereby significantly reducing the response time of the measurements.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A sensor for detecting concentration of a component in a breath sample, the sensor comprising a gas sampling cell comprising:
   an inlet;
   an outlet;
   a light source;
   a first light detector;
   a sampling channel configured to receive gas samples from the inlet and comprising a length extending from a first end to a second end of the sampling channel; the sampling channel defining an optic path along the length between the light source and the first light detector, wherein the light source is positioned adjacent to the first end and the first light detector is positioned adjacent to the second end; and a volume occupying material located within the sampling channel, wherein the volume occupying material extends the length of the sampling channel from the first end to the second end, the volume occupying material having an absorption coefficient for mid-infra-red light below 0.5 $cm^{-1}$.

2. The sensor of claim 1, wherein the volume occupying material having an absorption coefficient for mid-infra-red light below 0.3 $cm^{-1}$.

3. The sensor of claim 1, wherein the volume occupying material having an absorption coefficient for mid-infra-red light below 0.1 $cm^{-1}$.

4. The sensor of claim 1, wherein the volume occupying material occupies between 25%-75% of the volume of the sampling channel.

5. The sensor of claim 1, wherein the volume occupying material occupies between 35%-65% of the volume of the sampling channel.

6. The sensor of claim 1, wherein the volume occupying material comprises sapphire, silicone, germanium or any combination thereof.

7. The sensor of claim 1, wherein the light source is an infra-red (IR) light source.

8. The sensor of claim 1, wherein the first light detector comprises a first optical filter.

9. The sensor of claim 8, wherein the first light detector comprise a second optical filter; wherein the first optical filter is configured to transmit light having a first wavelength; and wherein the second optical filter is configured to transmit light having a second wavelength.

10. The sensor of claim 8, wherein the gas sampling cell further comprises a reference light detector.

11. The sensor of claim 10, wherein the reference light detector comprise a first and a second optical filter; wherein the first optical filter is configured to transmit light having a first wavelength; wherein the second optical filter is configured to transmit light having a second wavelength.

12. The sensor of claim 10, wherein a path length between the light source and the first light detector and/or the reference light detector is in the range of 5-15 mm.

13. The sensor of claim 10, wherein a distance between a first end of the volume occupying material and the light source is less than 5 mm.

14. The sensor of claim 10, wherein a distance between a second end of the volume occupying material and the first light detector and/or the reference light detector is less than 5 mm.

15. The sensor of claim 1, wherein a wall of the volume occupying material is covered with a reflective material.

16. The sensor of claim 1, wherein a wall of the sampling channel is covered with a reflective material.

17. The sensor of claim 1, wherein the gas sampling cell is devoid of a reference channel.

18. The sensor of claim 1, wherein the component is $CO_2$.

19. The sensor of claim 1, wherein the component is Nitric Oxide.

* * * * *